United States Patent
Hsieh

(10) Patent No.: US 9,970,960 B2
(45) Date of Patent: May 15, 2018

(54) SLIDING RAIL TYPE PROBE

(71) Applicant: CHUNGHWA PRECISION TEST TECH. CO., LTD., Taoyuan (TW)

(72) Inventor: Chih-Peng Hsieh, Taoyuan (TW)

(73) Assignee: CHUNGHWA PRECISION TEST TECH. CO., LTD., Taoyuan (TW)

( * ) Notice: Subject to any disclaimer, the term of this patent is extended or adjusted under 35 U.S.C. 154(b) by 0 days. days.

(21) Appl. No.: 15/439,967

(22) Filed: Feb. 23, 2017

(65) Prior Publication Data

US 2018/0074095 A1 Mar. 15, 2018

(30) Foreign Application Priority Data

Sep. 12, 2016 (TW) .............................. 105129631 A

(51) Int. Cl.
| | |
|---|---|
| *G01R 31/00* | (2006.01) |
| *G01R 1/067* | (2006.01) |
| *G01R 31/28* | (2006.01) |
| *G01N 1/00* | (2006.01) |

(52) U.S. Cl.
CPC ..... *G01R 1/06794* (2013.01); *G01R 1/06722* (2013.01); *G01R 31/2831* (2013.01); *G01N 1/00* (2013.01); *G01N 2201/00* (2013.01); *H01L 2221/00* (2013.01)

(58) Field of Classification Search
CPC ...... G01N 1/00; G01N 2201/00; H01L 21/00; H01L 2221/00; G01R 1/00
See application file for complete search history.

(56) References Cited

U.S. PATENT DOCUMENTS

| | | | | |
|---|---|---|---|---|
| 7,126,361 | B1 * | 10/2006 | Anderson | G01R 1/07342 |
| | | | | 324/750.08 |
| 2004/0250434 | A1 * | 12/2004 | Ogura | F16F 7/01 |
| | | | | 33/503 |
| 2009/0151182 | A1 * | 6/2009 | Chang | F16C 29/025 |
| | | | | 33/551 |
| 2010/0213960 | A1 * | 8/2010 | Mok | G01R 31/2889 |
| | | | | 324/762.03 |
| 2011/0266108 | A1 * | 11/2011 | Kitaguchi | B60L 5/42 |
| | | | | 191/22 C |
| 2015/0285608 | A1 * | 10/2015 | Singh | G01B 5/008 |
| | | | | 33/503 |

* cited by examiner

*Primary Examiner* — Jermele M Hollington
*Assistant Examiner* — Temilade Rhodes-Vivour
(74) *Attorney, Agent, or Firm* — Mark M. Friedman

(57) ABSTRACT

A probe having a sliding rail is provided and includes a probe head, a probe tail, an elastic element made of an elastic material and connected between the probe head and the probe tail, and a sliding rail assembly. The sliding rail assembly includes a slide rail and a position limit protrusion. The slide rail has a fixed end and a free end. The fixed end is fixedly connected to the probe tail, and the free end extends to the probe head. The position limit protrusion is fixedly connected to the probe head, and has a sliding slot formed thereon through which the slide rail can pass. The sliding rail assembly is made of a conductive material, and a cross-section area of the slide rail is greater than a cross-section area of the elastic material of the elastic element.

13 Claims, 4 Drawing Sheets

SLIDING RAIL TYPE PROBE

FIELD OF THE DISCLOSURE

The present disclosure relates to a probe, and more particularly to a probe used in a vertical probe card, and the probe includes a sliding rail.

BACKGROUND

Recently, with electronic products developing towards precision and versatility, the chip structure of integrated circuits used in electronic products tends to be complicated. At the time of manufacture, in order to ensure the electrical quality of the wafer, wafer-level measurement is performed before packaging the wafer. The current measuring method for testing wafers needs a probe card. According to the type of probes, probe card type includes a cantilever probe card and a vertical probe card. In use, the probes of the probe card are directly electrically contacted with pads or bumps of the wafer, and then an electrical signal is transmitted into a tester through a circuit board of the probe card, such that a testing signal from the tester is transmitted into the wafer, or an output signal from the wafer can be received by the tester, thereby achieving the measurement of the electrical properties of the wafer. Moreover, the user can remove a bad wafer according to the measurement results, so as to save unnecessary packaging costs.

FIG. 1 depicts a structural diagram of a spring probe 10 in the prior art. The spring probe 10 includes a probe head 11 and an elastic element 12. A terminal of the elastic element 12 is welded with the probe head 11, and the other terminal of the elastic element 12 is used for assembling with a probe card. FIG. 2 depicts another structural diagram of a spring probe 20 in the prior art. The spring probe 20 includes a probe head 21, an elastic element 22, and a probe tail 23. The spring probe 20 is roughly similar to the spring probe 10, and the difference between them are that two terminals of the elastic element 22 of the spring probe 20 are welded with the probe head 21 and the probe tail 23, respectively, and another terminal of the probe tail 23 is used for assembling with a probe card. Furthermore, the spring probe 20 may include a position sleeve (not shown in the drawing), which is sleeved onto the elastic element 22 for limiting the elastic element 22 to move forward and back in a straight line, thereby ensuring that there is no traverse movement in the corresponding position of the probe head 21 and the probe tail 23.

When measured by the conventional spring probe 10 or 20, the probe head 11 or 21 is firstly aligned with a pad or a bump of the wafer, and then applying a pressure to the spring probe 10 or 20 to ensure that the probe head 11 or 21 is effectively in electrical contact with the wafer, thereby transmitting current through the spring probe 10 or 20. That is, the current must be transmitted through the elastic element 12 or 22. However, in order to ensure the elastic deformation ability of the elastic element 12 or 22, the elastic material of the elastic element 12 or 22 must have a small cross-section area. Thus, if the current exceeds the maximum withstand current of the elastic elements 12 and 22, the elastic elements 12 and 22 may be deformed due to overheating that result in the so-called "needle burning". On the other hand, when the spring probes 10 and 20 perform high-speed signal transmission, since the transmission path of the elastic elements 12 and 22 is too long, an inductance effect is likely to occur, thereby affecting the signal quality.

Accordingly, it is necessary to provide an improving probe structure to solve the technical problem in the prior art.

SUMMARY OF THE DISCLOSURE

In order to solve the above-mentioned technical problems, an object of the present disclosure is to provide a probe including a conductive structure, which is connected between a probe head and a probe tail for transmitting current and signals. Moreover, since the conductive structure has a certain size cross-section area, the "needle burning" caused by the current exceeding the maximum withstand current of the conductive structure such that the conductive structure is deformed due to overheating can be prevented. Furthermore, the conductive structure is formed with the straight line configuration without bending, so that the current and the signal are transmitted through the straight path of the conductive structure. Hence, the high frequency and high speed transmission can be achieved and the inductance generated from transmitting the signal is relatively small.

In order to achieve the above object, the present disclosure provides a sliding rail type probe, including: a probe head; a probe tail disposed on a same axis as the probe head, and the probe tail and the probe head being disposed apart from each other; an elastic element made from elastic material and connected between the probe head and the probe tail, wherein the elastic element moves along a straight line when a force is either applied to or released from the probe head; and a sliding rail assembly, comprising: at least one slide rail including a fixed end and a free end, wherein the fixed end is fixedly connected with the probe tail, and the free end extends to the probe head; and a position limit protrusion fixedly connected with the probe head and including a sliding slot formed thereon through which the at least one slide rail can pass, wherein the sliding rail assembly is made from conductive material, and a cross-section area of the at least one slide rail is greater than a cross-section area of the elastic material of the elastic element.

In one preferable embodiment of the present disclosure, the fixed end of the at least one slide rail connects to an outer surface of the probe tail, and the position limit protrusion is fixedly connected to an outer surface of the probe head, and the at least one slide rail is a linear structure without bending, such that when the elastic element moves along the straight line, the probe head and the position limit protrusion move together along the at least one slide rail.

In one preferable embodiment of the present disclosure, the position limit protrusion comprises a base and a top plate, one end of the base is connected to the probe head and the other end of the base is connected with the top plate.

In one preferable embodiment of the present disclosure, a width of the top plate of the position limit protrusion is greater than a width of the base, and the sliding slot of the position limit protrusion is formed by outer surfaces of the top plate, the base, and the probe head.

In one preferable embodiment of the present disclosure, the at least one slide rail is disposed between the top plate of the position limit protrusion and an outer surface of the probe head, and the at least one slide rail electrically contacts either at least one of an outer surface of the top plate or the outer surface of the probe head.

In one preferable embodiment of the present disclosure, the sliding rail assembly includes an inner conductive material and an outer conductive material, and the outer conductive material covers the inner conductive material.

In one preferable embodiment of the present disclosure, a conductivity of the outer conductive material is greater than a conductivity of the inner conductive material, and a hardness of the inner conductive material is greater than a hardness of the outer conductive material.

In one preferable embodiment of the present disclosure, the outer conductive material and the inner conductive material are selected from one group consisting of metal and graphite.

In one preferable embodiment of the present disclosure, the outer conductive material is made from metal and is selected from one group consisting of gold, silver, alloys and the combinations thereof, and wherein the inner conductive material is made from metal and is selected from one group consisting of copper, iron, alloys and the combinations thereof.

In one preferable embodiment of the present disclosure, the probe head and the probe tail are either cylindrical structures or plate-type structures.

In one preferable embodiment of the present disclosure, the probe head includes a probe tip which is formed of one group consisting of a flat shape, a rounded shape, a point-like shape, or a multi-claw shape.

In one preferable embodiment of the present disclosure, the sliding rail assembly includes a pair of slide rails, and the position limit protrusion includes a pair of sliding slots through which the pair of slide rails can pass, and the pair of slide rails electrically contacts with the position limit protrusion.

In one preferable embodiment of the present disclosure, the position limit protrusion is formed in a T-shaped configuration including having a base formed in an I-shaped configuration and a top plate formed in a flat-shaped configuration, and a first end of the base is connected to the probe head, and a second end of the base is connected with the top plate; and wherein the pair of sliding slots is located at two sides of the T-shaped configuration, respectively.

DETAILED DESCRIPTION

The structure and the technical means adopted by the present disclosure to achieve the above and other objects can be best understood by referring to the following detailed description of the preferred embodiments and the accompanying drawings.

Figure 1:
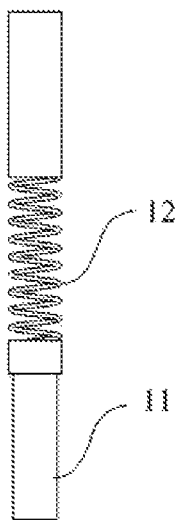
FIG. 1 depicts a structural diagram of a spring probe in the prior art.
Figure 2:
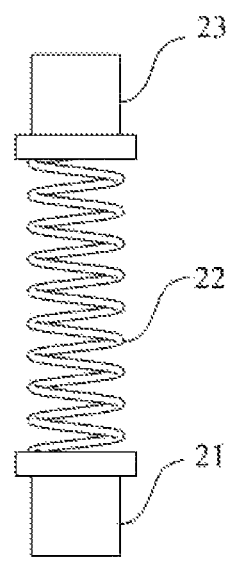
FIG. 2 depicts another structural diagram of a spring probe in the prior art.
Figure 3:
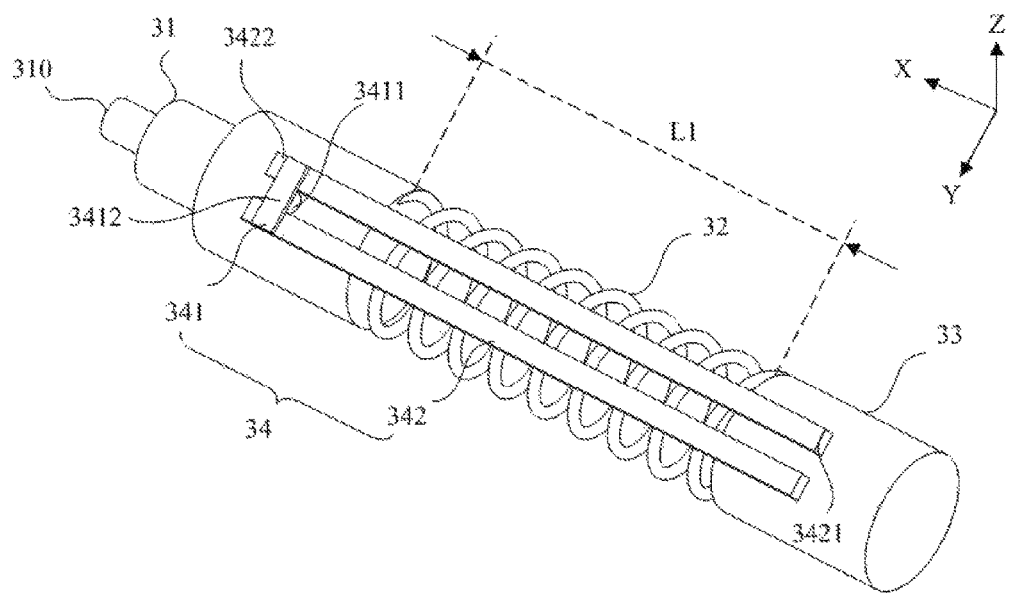
FIG. 3 depicts a stereoscopic diagram of a sliding rail type probe according to a first preferred embodiment of the present disclosure.

FIG. 3 depicts a stereoscopic diagram of a sliding rail type probe 30 according to a first preferred embodiment of the present disclosure. The sliding rail type probe 30 is used for assembling with a probe device of a probe card. The sliding rail type probe 30 includes a probe head 31, an elastic element 32, a probe tail 33, and a sliding rail assembly 34. The probe head 31 and the probe tail 33 are disposed in alignment with the same axis (i.e., X axis) and they are separated from each other. The probe head 31 and the probe tail 33 may be cylindrical (as shown in FIG. 3), a geometrical configuration, or a plate configuration in shape. The probe head 31 includes a probe tip 310 which is formed with a flat shape (as shown in FIG. 3), a rounded shape, a point-like shape, or a multi-claw shape, but the present disclosure is not limited thereto.

As shown in FIG. 3, the elastic element 32 is made of elastic material, and is connected between the probe head 31 and the probe tail 33. The elastic element 32 can be move along a straight line (e.g., a line in the X-direction), such as a reciprocating movement. Preferably, the probe head 31 and the probe tail 33 are melded with the elastic element 32. In use, the probe tail 33 of the sliding rail type probe 30 is electrically connected to a pad (e.g., a metallic pad, a metallic bump, a solder ball, etc.) of a circuit board of the probe card. Moreover, the probe head 31 of the sliding rail type probe 30 is electrically connected with a corresponding pad or bump of a device under test (e.g., a wafer). By electrically connecting the sliding rail type probe 30 of the probe card with the corresponding pad or bump of the device under test, an electrical signal is transmitted to a tester via the circuit board of the probe card, such that a testing signal from the tester is transmitted into the device under test, or an output signal from the device under test can be received by the tester, thereby achieving the measurement of the electrical properties of the device under test. Moreover, the user can remove a bad device under test according to the measurement results, so as to save unnecessary packaging costs.

As shown in FIG. 3, the sliding rail assembly 34 includes a pair of slide rails 342 and a position limit protrusion 341. Each of slide rails 342 is formed with a linear structure without bending, and includes a fixed end 3421 and a free end 3422. The fixed end 3421 is fixedly connected with (e.g., melded with) an outer surface of the probe tail 3421, and the free end 3422 extends to the probe head 31. The position limit protrusion 341 includes a base 3411 and a top plate 3412. A terminal of the base 3411 is fixedly connected with (e.g., melded with) an outer surface of the probe head 31, and another terminal of the base 3411 is connected with the top plate 3412. Preferably, the base 3411 and the top plate 3412 are integrally formed. A pair of sliding slots 3413 (referring to FIG. 5) for free ends 3422 of the pair of slide rails 342 to pass through is formed on the position limit protrusion 341 of the sliding rail assembly 34. Moreover, a move direction of the slide rail 342 can be effectively restricted by the sliding slot 3413 of the position limit protrusion 341. To be specific, as shown on FIG. 5, since a width D2 of the top plate 3412 of the position limit protrusion 341 is greater than a width D1 of the base 3411, the outer surface of the top plate 3412, the base 3411, and the probe head 31 will connected with each other to define the pair of sliding slots 3413 of the position limit protrusion 341. For example, in the first preferred embodiment of the present disclosure, the position limit protrusion 341 is formed in a T-shaped configuration including a base 3411 formed in an I-shaped configuration and a top plate 3412 formed in a flat-shaped configuration, and a first end of the base 3411 is connected to the probe head 3412, and a second end of the base 3411 is connected with the top plate 3412. The pair of sliding slots 3413 is disposed at two sides of the T-shaped configuration, respectively. It should be noted that in another embodiment, the position limit protrusion may be formed with a different configuration, and the number of the slide rails and the sliding slots are not limited to two. In addition, the probe head 31 of the sliding rail type probe 30, the probe tail 33, and the sliding rail assembly 34 are made of conductive material, such as metal, graphite, and so on. Also, the pair of slide rail 342 will be electrically contacted with at least one of an outer surface of the top plate 3412 or the probe head 31.

Figure 4:
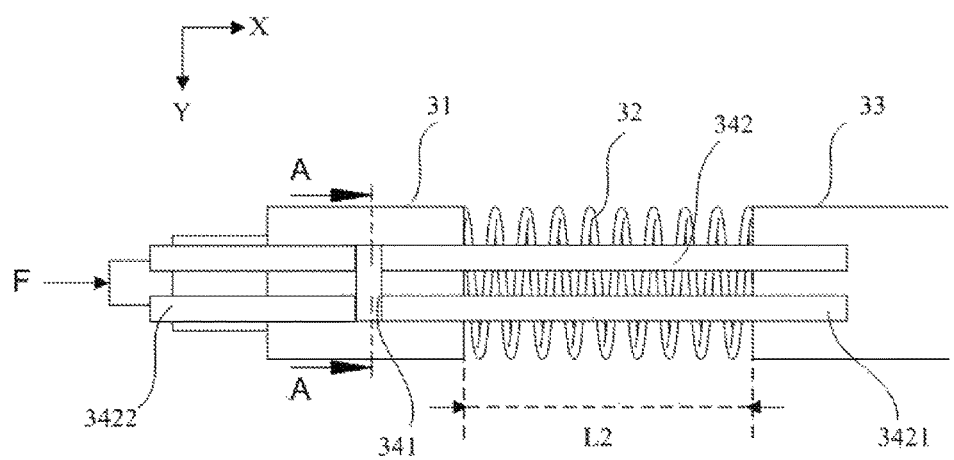
FIG. 4 depicts a diagram of a sliding rail type probe of FIG. 3 after applying a pressure.

FIG. 4 depicts a diagram of a sliding rail type probe of FIG. 3 after applying a pressure. The pair of slide rails 342 is disposed between the top plate 3412 of the position limit protrusion 341 and the outer surface of the probe head 31. The probe head 31 can be moved along the pair of slide rails 342. Due to the free end 3422 of the slide rail 342 not being fixedly connected with the probe head 31, the probe head 31 and the position limit protrusion 341 will move together with the elastic element 32 along the pair of slide rails 342. Specifically, when a force F is applied on the sliding rail type probe 30, the elastic element 32 undergoes compressed elastic deformation, and a relative position between the free end 3422 of the slide rail 342 and the probe head 31 will be changed. After releasing the force F, the relative position between the free end 3422 of the slide rail 342 and the probe head 31 will be changed accordingly. It should be understood that since there is no structural interference between the elastic element 32 and the slide rail 342, the pair of slide rails 342 is free to slide in the pair of sliding slots 3413 of the position limit protrusion, thereby ensuring the elastic element 32 can be smoothly operated.

When a wafer is tested by a probe card having the sliding rail type probe 30, the probe head 31 is firstly aligned with a pad or a bump of the wafer, and then the force F is applied to the sliding rail type probe 30, such that the elastic element 32 is elastically deformed (i.e., the length of the elastic element 32 is shortened from L1 to L2) to ensure that the probe head 31 is effectively in electrical contact with the wafer, thereby transmitting current through the sliding rail assembly 34. That is, the current is transmitted by the probe head 31, the probe tail 33, and the sliding rail assembly 34.

Figure 5:
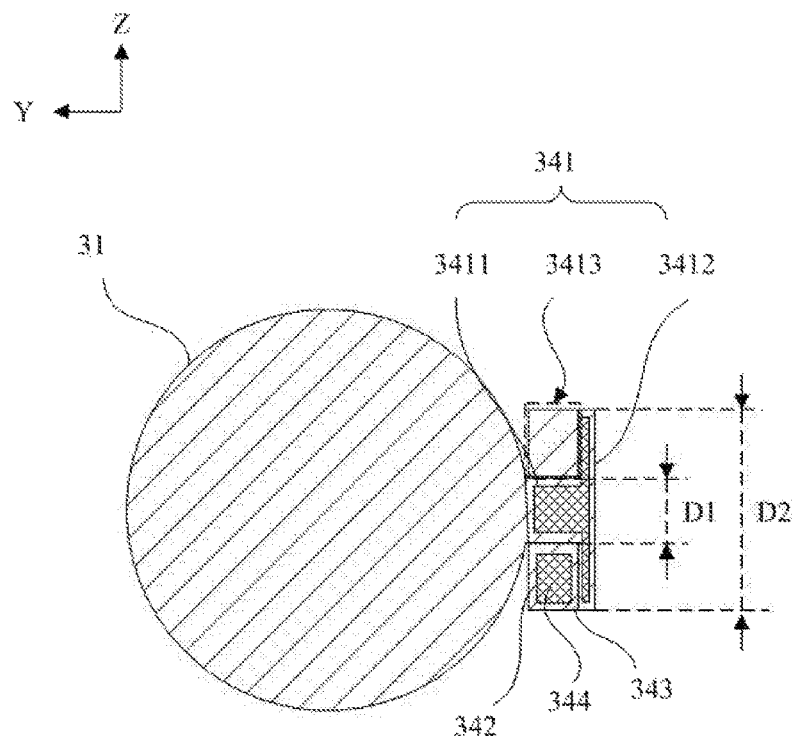
FIG. 5 depicts a cross-section along A-A of FIG. 4.

FIG. 5 depicts a cross-section along A-A of FIG. 4. The position limit protrusion 341 and the pair of slide rails 342 is formed by an inner conductive material 344 and an outer conductive material 343. The inner conductive material 344 is covered by the outer conductive material 343. The inner conductive material 344 and the outer conductive material 343 may include metal or graphite. It should be noted that due to the skin effect, the transmitting current will be concentrated on the surface of the conductor. Thus, in the present disclosure, in order to enhance the transfer efficiency of the current, the outer conductive material 343 is made of a material having a high electrical conductivity with respect to the inner conductive material 344. Furthermore, in order to improve the strength of the overall structure, the inner conductive material 344 is made of a material having a relatively high hardness relative to the outer conductive 343. Preferably, the outer conductive material 343 may be made of a material having high electrical conductivity, such as gold or silver or alloys thereof. Moreover, the inner conductive material 344 may be made of a material having high hardness, such as copper or iron or alloys thereof.

The elastic element 32 may be made of either conductive material or insulating material. If the elastic element 32 is made of insulating material, the current can still be smoothly transmitted on the sliding rail type probe 30. Furthermore, the cross-section area of the slide rail 342 of the sliding rail assembly 34 is greater than the cross-section area of the elastic material of the elastic element 32 as viewed from a cross-section (i.e., Y-Z plane). Thus, if the elastic element 32 is made of conductive material, the current is also primarily transmitted by the sliding rail assembly 34, and the elastic element 32 can further exhibit the function of sharing the current transfer. In addition, in order to form the sliding rail type probe 30 having a small configuration and a high degree of coplanarity and high precision, the present disclosure preferably uses microelectromechanical systems (MEMS) technology to manufacture the sliding rail type probe 30. Furthermore, the probe head 31 and the sliding rail assembly 34 are manufactured by a combination of lithography and electroplating, the configuration of the position limit protrusion 341 of the sliding rail assembly 34 can be effectively adjusted, thereby controlling the sliding direction of the slide rail 342. Moreover, the electrical contact area of the slide rail 342 with at least one of both the probe head 31 and the position limit protrusion 341 can be effectively increased.

As described above, in the present disclosure, since the current is transmitted by the sliding rail assembly 34 having a large cross-section area, rather than by the elastic material of the elastic element 32 (as shown in FIG. 3, the coil spring structure), the "needle burning" caused by the current exceeding the maximum withstand current of the elastic element 32 such that the coil spring structure is deformed due to overheating can be prevented. In addition, since the signal is transmitted through the linear path of the slide rail 342, instead of by the spiral path of the elastic element 32, the transmission path of the signal is effectively shortened, and the effect of high frequency and high speed transmission is achieved, and the inductance resulting from signal transmission is also relatively small.

Figure 6:
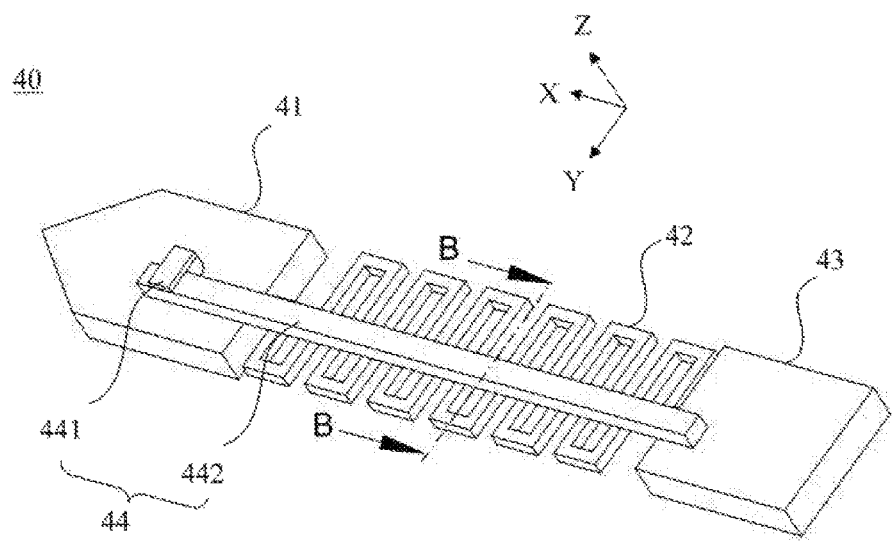
FIG. 6 depicts a stereoscopic diagram of a sliding rail type probe according to a second preferred embodiment of the present disclosure.

FIG. 6 depicts a stereoscopic diagram of a sliding rail type probe 40 according to a second preferred embodiment of the present disclosure. The sliding rail type probe 40 includes a probe head 41, an elastic element 42, a probe tail 43, and a sliding rail assembly 44. The difference between the sliding rail type probe 40 of the second preferred embodiment and the sliding rail type probe 30 of the first preferred embodiment is the probe head 31 and the probe tail 33 of the sliding rail type probe 30 of the first preferred embodiment are form with a cylindrical structure, and the probe head 41 and the probe tail 43 of the sliding rail type probe 40 are formed with a plate-type structure. Also, the elastic material of the elastic element 32 of the first preferred embodiment has a three-dimensional spiral structure, whereas the elastic material of the elastic element 42 of the second preferred embodiment has a two-dimensional bending structure. It can be understood that the operating mechanism of the sliding rail type probe 40 of the second preferred embodiment is similar to that of the sliding type probe 30 of the first preferred embodiment, and is not described here again. In addition, the sliding rail assembly 44 of the second preferred embodiment utilizes a single slide rail 442, but it is also possible to utilize a dual slide rail. It will be understood that the operating mechanism of the sliding mechanism assembly 44 of the second preferred embodiment of the present disclosure is the same as the sliding rail assembly 34 of the first preferred embodiment of the present disclosure and is not described in detail herein.

Figure 7:
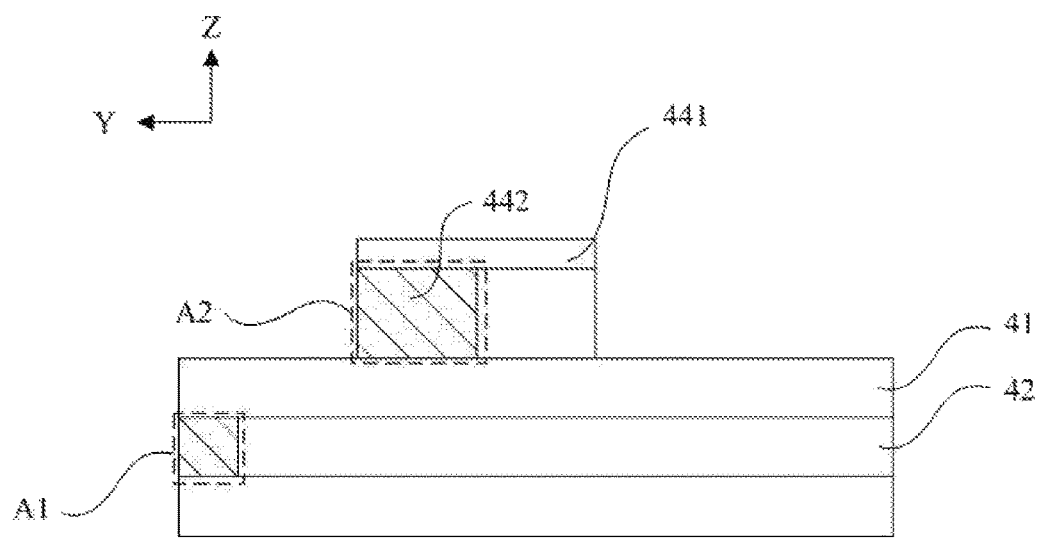
FIG. 7 depicts a cross-section along B-B of FIG. 6.

FIG. 7 depicts a cross-section along B-B of FIG. 6. The sliding rail assembly 44 includes a position limit protrusion 441 and a slide rail 442, which are made of conductive material, and preferably comprise a double-layer conductive structure (such as the inner conductive material 344 and the outer conductive material 343 of the first preferred embodiment). Furthermore, the probe head 41 and the probe tail 43 of the sliding rail type probe 40 are also made of conductive material (e.g., metal or graphite). Also, the cross-section area A2 of the slide rail 442 of the sliding rail assembly 44 is greater than the cross-section area A1 of the elastic material of the elastic element 42 as viewed from a cross-section (i.e., Y-Z plane). That is, in the present disclosure, since the current is transmitted by the sliding rail assembly 44 having a large cross-section area, rather than by the elastic material of the elastic element 42 (such as the two-dimensional bending elastic structure as shown in FIG. 6), it is possible to prevent "needle burning" caused by the current exceeding the maximum withstand current of the elastic element 42 such that the bending elastic structure of the elastic element 42 will be deformed due to overheating. In addition, since the signal is transmitted through the liner path of the slide rail 442, instead of by the bending path of the elastic element 42, the signal transmission path is effectively shortened, and the effect of high frequency and high speed transmission is achieved, and the inductance resulting from signal transmission is also relatively small.

The above descriptions are merely preferable embodiments of the present disclosure, and are not intended to limit the scope of the present disclosure. Any modification or replacement made by those skilled in the art without departing from the spirit and principle of the present disclosure should fall within the protection scope of the present disclosure. Therefore, the protection scope of the present disclosure is subject to the appended claims.

What is claimed is:

1. A sliding rail type probe, comprising:
   a probe head;
   a probe tail disposed on a same axis as the probe head, and the probe tail and the probe head being disposed apart from each other;
   an elastic element made from elastic material and connected between the probe head and the probe tail, wherein the elastic element moves along a straight line when a force is either applied to or released from the probe head; and
   a sliding rail assembly, comprising:
      at least one slide rail comprising a fixed end and a free end, wherein the fixed end is fixedly connected with the probe tail, and the free end extends to the probe head; and
      a position limit protrusion fixedly connected with the probe head and comprising a sliding slot formed thereon through which the at least one slide rail can pass,
   wherein the sliding rail assembly is made from conductive material, and a cross-section area of the at least one slide rail is greater than a cross-section area of the elastic element.

2. The sliding rail type probe as claimed in claim 1, wherein the fixed end of the at least one slide rail connects to an outer surface of the probe tail, and the position limit protrusion is fixedly connected to an outer surface of the probe head, and the at least one slide rail is a linear structure without bending, such that when the elastic element moves along the straight line, the probe head and the position limit protrusion move together along the at least one slide rail.

3. The sliding rail type probe as claimed in claim 1, wherein the position limit protrusion comprises a base and a top plate, one end of the base is connected to the probe head and the other end of the base is connected with the top plate.

4. The sliding rail type probe as claimed in claim 3, wherein a width of the top plate of the position limit protrusion is greater than a width of the base, and the sliding slot of the position limit protrusion is formed by outer surfaces of the top plate, the base, and the probe head.

5. The sliding rail type probe as claimed in claim 3, wherein the at least one slide rail is disposed between the top plate of the position limit protrusion and an outer surface of the probe head, and the at least one slide rail electrically contacts either at least one of an outer surface of the top plate or the outer surface of the probe head.

6. The sliding rail type probe as claimed in claim 1, wherein the sliding rail assembly comprises an inner conductive material and an outer conductive material, and the outer conductive material covers the inner conductive material.

7. The sliding rail type probe as claimed in claim 6, wherein a conductivity of the outer conductive material is greater than a conductivity of the inner conductive material, and a hardness of the inner conductive material is greater than a hardness of the outer conductive material.

8. The sliding rail type probe as claimed in claim 6, wherein the outer conductive material and the inner conductive material are selected from one group consisting of metal and graphite.

9. The sliding rail type probe as claimed in claim 8, wherein the outer conductive material is made from metal and is selected from one group consisting of gold, silver, alloys and the combinations thereof, and wherein the inner conductive material is made from metal and is selected from one group consisting of copper, iron, alloys and the combinations thereof.

10. The sliding rail type probe as claimed in claim 1, wherein the probe head and the probe tail are either cylindrical structures or plate-type structures.

11. The sliding rail type probe as claimed in claim 1, wherein the probe head includes a probe tip which is formed of one group consisting of a flat shape, a rounded shape, a point-like shape, or a multi-claw shape.

12. The sliding rail type probe as claimed in claim 1, wherein the sliding rail assembly comprises a pair of slide rails, and the position limit protrusion comprises a pair of sliding slots through which the pair of slide rails can pass, and the pair of slide rails electrically contact with the position limit protrusion.

13. The sliding rail type probe as claimed in claim 12, wherein the position limit protrusion is formed in a T-shaped configuration having a base formed in an I-shaped configuration and a top plate formed in a flat-shaped configuration, and a first end of the base is connected to the probe head, and a second end of the base is connected with the top plate, and wherein the pair of sliding slots is disposed at two sides of the T-shaped configuration, respectively.

* * * * *